United States Patent [19]

Kreighbaum et al.

[11] 4,015,006
[45] Mar. 29, 1977

[54] 3(2H)-ISOQUINOLONES THERAPEUTIC PROCESS

[75] Inventors: William E. Kreighbaum; William T. Comer, both of Evansville, Ind.

[73] Assignee: Mead Johnson & Company, Evansville, Ind.

[22] Filed: Sept. 12, 1975

[21] Appl. No.: 612,884

Related U.S. Application Data

[62] Division of Ser. No. 423,841, Dec. 11, 1973, Pat. No. 3,910,927, which is a division of Ser. No. 184,197, Sept. 27, 1971, Pat. No. 3,798,225.

[52] U.S. Cl. .................................... 424/258
[51] Int. Cl.$^2$ .............................. A61K 31/47
[58] Field of Search ............................ 424/258

[56] References Cited

UNITED STATES PATENTS

| 2,683,713 | 7/1954 | Shepard | 260/289 R |
| 2,728,769 | 12/1955 | Shepard | 260/289 R |

OTHER PUBLICATIONS

Dorofeenko, et al. Jour. Gen. Chem. USSR, vol. 40, p. 230 (1970).
Elliott, Jour. Hetero. Chem., vol. 7, pp. 1229–30 (1970).

*Primary Examiner*—Albert T. Meyers
*Assistant Examiner*—Daren M. Stephens
*Attorney, Agent, or Firm*—Robert H. Uloth; Robert E. Carnahan

[57] ABSTRACT

New 2-substituted-3(2H)-isoquinolones and 2-substituted-3-alkoxyisoquinolines are disclosed. They are orally active hypotensives and peripheral vasodilators with an extended duration of action. Representative embodiments of this invention are 6,7-dimethoxy-2-methyl-1-veratryl-3(2H)-isoquinolone hydrochloride, 2-allyl-6,7-dimethoxy-1-veratryl-3(2H)-isoquinolone hydrochloride, 2-cyclopropyl-6,7-dimethoxy-1-veratryl-3(2H)-isoquinolone hydrochloride, 2-amino-6,7-dimethoxy-1-veratryl-3(2H)-isoquinolone hydrochloride, and 3-ethoxy-6,7-dimethoxy-1-veratrylisoquinoline.

15 Claims, No Drawings

3(2H)-ISOQUINOLONES THERAPEUTIC PROCESS

CROSS REFERENCE TO RELATED APPLICATIONS

This patent application is a divisional of U.S. patent application Ser. No. 423,841 filed Dec. 11, 1973 and now U.S. Pat. No. 3,910,927, which in turn is a divisional of U.S. patent application Ser. No. 184,197 filed Sept. 27, 1971 and now U.S. Pat. No. 3,798,225.

BACKGROUND OF THE INVENTION

This invention is concerned with certain heterocyclic carbon compounds having one hetero-N-atom. More particularly, it relates to 3(2H)-isoquinolones and 3-alkoxyisoquinolines which have hypotensive and peripheral vasodilating properties. Although the compounds of the present invention are of the same basic ring system as the isoquinoline, 6,7-dimethoxy-1-veratryl-3-isoquinolinol described by G. N. Dorofeenko and V. G. Korobkova, J. Gen. Chem., USSR., 40, 230 (1970), they differ substantially in biological activity. Thus, for example, the compounds of the present invention are active orally as hypotensive and peripheral vasodilating agents whereas the prior art isoquinolinol is essentially inactive.

SUMMARY OF THE INVENTION

The present invention is concerned with novel 2-substituted-3(2H)-isoquinolones of Formula I and 3-alkoxy-isoquinolines of Formula II and with non-toxic pharmaceutically acceptable acid addition salts thereof. These subtances have utility as peripheral vasodilators and hypotensive agents.

It is to be understood that the terms "lower alkyl" and "lower alkoxy" when used herein contemplates both straight and branched chain groups, containing from 1 to about 4 carbon atoms. Illustrative of such groups are methyl, ethyl, propyl, isopropyl, 1-butyl, 1-methylpropyl, 2-methylpropyl, tert.-butyl, and the corresponding alkoxy groups. The term "halogen" includes chlorine, bromine, iodine and fluorine.

The alkenyl groups referred to herein are straight or branched chains having from 3 to 6 carbon atoms and are illustrated by the formulas following.

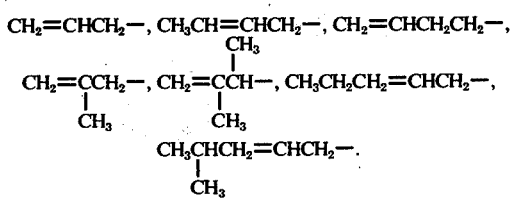

It is to be understood that the term "non-toxic pharmaceutically acceptable acid addition salts" used herein and in the appended claims denotes a combination of the 3(2H)-isoquinolones and isoquinolines of Formulas I and II with suitable non-toxic inorganic or organic acids to provide salts having physical properties including requisite stability adaptable for pharmaceutical formulations. Examples of non-toxic pharmaceutically acceptable acid addition salts of the compounds of Formulas I and II are those formed with sulfuric, hydrochloric, phosphoric, hydrobromic, hydroiodic, sulfamic, methanesulfonic, benzenesulfonic, para-toluenesulfonic, acetic, lactic, succinic, malic,

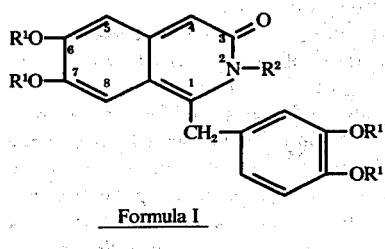

Formula I

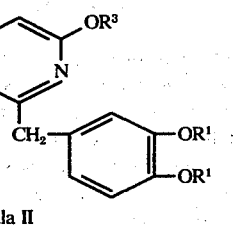

Formula II

In Formulas I and II above, $R^1$ represents lower alkyl. The $R^2$ "N-substituent" identifies a member of the group consisting of hydroxy, lower alkoxy, amino, lower alkylamino, lower dialkylamino, lower alkyl, alkenyl, cycloalkyl of from 3 to 5 carbon atoms inclusive, and phenylalkyl having up to 10 carbon atoms. Said phenylalkyl may have substituents attached to the phenyl ring which are selected from halogen, lower alkyl, methylenedioxy, and up to 3 lower alkoxy groups. $R^3$, in Formula II, represents lower alkyl, alkenyl, cycloalkyl of from 3 to 5 carbon atoms inclusive, and benzyl.

maleic, mucic, tartaric, citric, gluconic, benzoic, cinnamic, isethionic, fumaric, and related acids.

The 3(2H)-isoquinolones of Formula I and acid addition salts thereof have a distinctive light to deep yellow color in the solid state. This color is attributed to the ortho-quinoid structure as represented by Formula I. The ortho-quinoid structure is consistent with ultraviolet, nuclear magnetic reasonance, and infrared spectra for the 3(2H)-isoquinolones of Formula I rather than other tautomeric forms such as those represented by Formula Ia and Formula Ib. Formula Ia in which $R^1$ and $R^2$ are methyl groups has been reported by I. W. Elliott, J. Heterocycl. Chem., 7, 1229–1230 (1970).

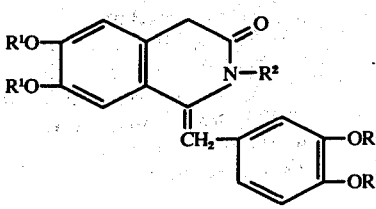

Formula Ia

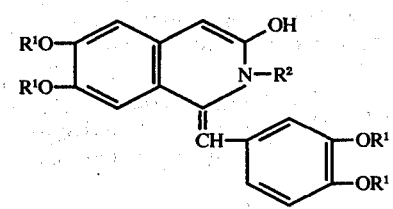

Formula Ib

A variety of methods may be employed to produce the novel isoquinolones of this invention. One particularly preferred method is the condensation of an $R^2$-$NH_2$ intermediate with a lactone corresponding to Formula III wherein $R^1$ and $R^2$ have the meaning given above.

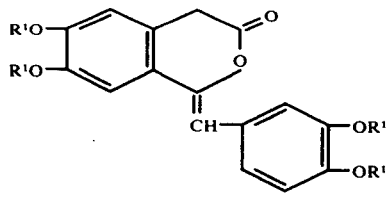

Formula III

The condensation is carried out in an inert organic solvent as a reaction medium. Tetrahydrofuran is a preferred solvent but other solvents such as benzene, toluene, dioxane, acetonitrile, chloroform and the like are also useful. Preferably, the reaction is conducted at about 25° C., although this temperature is not critical and reaction temperatures appreciably above and below are also operable. After the condensation is complete, the solvent is evaporated and the residue treated with hydrochloric acid to provide a hydrochloride salt of the isoquinolones of Formula I. Other nontoxic pharmaceutically acceptable acid addition salts may be prepared by treating the residue with other suitable organic or inorganic acids.

Acid addition salts of the present invention can be converted to the corresponding free bases by reaction with a basic reagent such as aqueous ammonia. Although both the free base and salt forms of the compounds of the present invention are useful for the purposes of the invention, salts are generally preferred as they are relatively more stable than free base forms.

The lactone condensation probably involves formation of 1-hydroxy-3(2H)-isoquinolone intermediates which in presence of acid undergo dehydration to form 3(2H)-isoquinolones of Formula I. Illustrative of such an intermediate is 1,4-dihydro-1-hydroxy-6,7-dimethoxy-2-methyl-1-veratryl-3(2H)-isoquinolone which is obtained by the condensation of methylamine with the lactone, 1-(3,4-dimethoxybenzylidene)-6,7-dimethoxy-3-isochromanone. In the presence of hydrochloric acid, this intermediate converts rapidly to 6,7-dimethoxy-2-methyl-1-veratryl-3(2H)-isoquinolone hydrochloride.

Lactones identified by general Formula III above are obtained by dehydrating keto acids of Formula IV wherein $R^1$ has the above meaning in a mixture of acetic anhydride, glacial acetic acid and concentrated sulfuric acid. This method is essentially that described by I. W. Elliott, supra, for the preparation of 1-(3,4-dimethoxybenzylidene)-6,7-dimethoxy-3-isochromanone from the keto acid 2-(3,4-dimethoxyphenylacetyl)-4,5-dimethoxyphenylacetic acid.

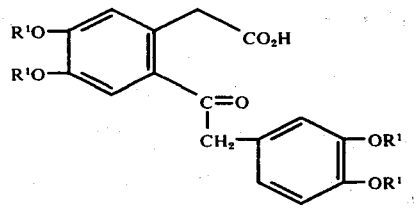

Formula IV

Keto acid intermediates of Formula IV are provided by intermolecular acylation of appropriate 3,4-dialkoxyphenylacetic acids in polyphosphoric acid at moderate temperatures of from about 25°-100° C. This method is known and is described by G. N. Dorofeenko and V. G. Korobkova, J. Gen. Chem., USSR., 40, 230 (1970) for the preparation of 2-(3,4-dimethoxyphenylacetyl)-4,5-dimethoxyphenylacetic acid from 3,4-dimethoxyphenylacetic acid. Illustrative of keto acids provided by this procedure are:
2-(3,4-dimethoxyphenylacetyl)-4,5-dimethoxyphenylacetic acid,
2-(3,4-diethoxyphenylacetyl)-4,5-diethoxyphenylacetic acid,
2-(3,4-diisopropoxyphenylacetyl)-4,5-diisopropoxyphenylacetic acid,
2-(3,4-di-n-butoxyphenylacetyl)-4,5-di-n-butoxyphenylacetic acid,
which are obtained from intermolecular acylation of the 3,4-dialkoxyphenylacetic acids:
3,4-dimethoxyphenylacetic acid,
3,4-diethoxyphenylacetic acid,
3,4-diisopropoxyphenylacetic acid,
3,4-di-n-butoxyphenylacetic acid.

Some of the isoquinolones of Formula I may also be produced by cyclization of keto acids of Formula IV with $R^2$—$NH_2$ intermediates in acetic acid.

An alternate method of preparing isoquinolones of general Formula I wherein $R^2$ is methyl is by alkylation of a 6,7-dialkoxy-1-(3,4-dialkoxybenzyl)-3-isoquinolinol with methyl iodide in the presence of a base such as sodium methoxide. The predominate product is the N-alkylated isoquinolone with a minor amount of a 3-methoxyisoquinoline of Formula II.

Another method of preparing 3-methoxyisoquinolines of Formula II is by alkylation of the silver salt of 6,7-dialkoxy-1-(3,4-dialkoxybenzyl)-3-isoquinolinols with methyl iodide.

Isoquinolines of Formula II are preferably obtained from corresponding 6,7-dialkoxy-1-(3,4-dialkoxybenzyl)-3-isoquinolinols by reaction with a $R^3X$-alkylating agent in a reaction inert organic solvent such as, e.g., benzene, toluene, dioxane and preferably acetone, at moderately high temperatures, e.g., between about 60° and 120° C. in the presence of bases, e.g., alkali metal carbonates such as potassium carbonate. $R^3$ is as defined above and the symbol X refers to the acid residue of a reactive ester grouping such as e.g., a bromide, iodide, chloride, sulfate, tosylate or mesylate.

An alternate method of preparing isoquinolines of Formula II is by alkylation of corresponding 6,7-dialkoxy-1-(3,4-dialkoxybenzyl)-3-isoquinolinols with a trialkyloxonium fluoroborate as described in L. F.

Fieser and M. Fieser, "Reagents for Organic Synthesis", page 1210 (Wiley, 1967).

The compounds of the present invention identified by Formulas I and II have hypotensive and peripheral vasodilating properties and are, therefore, useful in treating conditions in mammals responsive to administration of such agents. They are orally active and when compared to papaverine in the dog have a considerably longer duration of action.

These valuable pharmacological properties can be demonstrated by standard pharmacological methods. For example, hypotensive and peripheral vasodilating activity are measured in anesthetized dogs according to the following procedure. A tracheotomy is performed and the animal is ventilated mechanically and arranged for recording arterial blood pressure, aortic blood flow, right ventricular contractile force and heart rate. The test agent is administered by a rubber catheter inerted into the duodenum through the pyloric sphincter via a small incision in the stomach wall (duodenal administration is considered to be equivalent to oral administration by mouth or by stomach tube).

Illustrative of the cardiovascular activity exhibited by the compounds of the present invention in this test is that obtained with a preferred compound, 6,7-dimethoxy-2-methyl-1-veratryl-3(2H)-isoquinolone hydrochloride, which at a dose of 5 mg./kg. body weight produced a 30% decrease in diastolic blood pressure and a 19% decrease in total peripheral resistance. Mean systemic blood pressure divided by mean aortic blood flow is taken as a measure of total peripheral resistance. At a similar dose, both papaverine, which is a well known peripheral vasodilator and 6,7-dimethoxy-1-veratryl-3-isoquinolinol, a prior art isoquinoline, are devoid of significant cardiovascular activity.

Selective hypotensive and peripheral vasodilating effects relative to the ventricular contractile force and heart rate are produced by the instant compounds when compared to papaverine. That is to say, desirable hypotensive and peripheral vasodilating responses are obtained with substantially less adverse cardiac effects, e.g., increased ventricular contractile force and heart rate, than is produced by an effective dose of papaverine.

There can be mentioned by way of example the following compounds as those particularly preferred for oral hypotensive and peripheral vasodilating activity:
6,7-dimethoxy-2-methyl-1-veratryl-3(2H)-isoquinolone hydrochloride,
2-allyl-6,7-dimethoxy-1-veratryl-3(2H)-isoquinolone hydrochloride,
2-cyclopropyl-6,7-dimethoxy-1-veratryl-3(2H)-isoquinolone hydrochloride,
2-amino-6,7-dimethoxy-1-veratryl-3(2H)-isoquinolone hydrochloride.

The process of the present invention for producing a hypotensive and peripheral vasodilating effect in a mammal is carried out by systemic administration of an effective non-toxic dose of the 3(2H)-isoquinolones of Formula I and 3-alkoxyisoquinolines of Formula II ranging from about 0.05 to 20 mg./kg. body weight of the mammal. It is intended by systemic administration to include both oral and parenteral routes. Oral administration is preferred, although parenteral routes, e.g., intramuscular, intravenous, intraperitoneal and subcutaneous administration may also be employed. The dosage will vary with the form of administration and the particular compound chosen. Generally, the compound is administered at a dosage substantially less than the dose of the compound which is thought to be effective. Thereafter, in conformity with accepted therapeutic methods, the dosage is increased by small increments until the desired hypotensive or vasodilating effect is reached.

The compounds which constitute this invention and their methods for preparation will appear more fully from the consideration of the following examples which are given for the purpose of illustration only and are not to be construed as limiting the invention in spirit or scope.

EXAMPLE 1

6,7-Dimethoxy-2-Methyl-1-Veratryl-3(2H)-Isoquinolone Hydrochloride

A. Alkylation of 6,7-dimethoxy-1-veratryl-3-isoquinolinol.

Sodium methoxide (26.0 g., 0.48 mole) is added portion-wise to a refluxing suspension of 6,7-dimethoxy-1-veratryl-3-isoquinolinol (28.4 g., 0.08 mole), methyl iodide (224 g., 1.60 mole) and 400 ml. of methanol over a 24 hr. period. The consumption of the isoquinolinol is monitored by thin layer chromatography (silica gel developed in 9:1 chloroform methanol) and when complete the reaction is filtered and the filtrate concentrated. Residual oil which remains is taken up in ethyl acetate and washed with three 300 ml. portions of water. After drying over potassium carbonate, the ethyl acetate solution is filtered through decolorizing charcoal and acidified with 5N ethanolic hydrogen chloride to provide a yellow solid. Crystallization of this material from methanol-ethyl acetate affords analytically pure 6,7-dimethoxy-2-methyl-1-veratryl-3(2H)-isoquinolone hydrochloride, 13.8 g. (43%) m.p. 223.0°–225.0° C. (dec.)(corr.).

Analysis. Calcd. for $C_{21}H_{23}NO_5 \cdot HCl$ (percent): C, 62.14; H, 5.96; N, 3.45. Found (percent): C, 62.16; H, 5.96; N, 3.45.

Absorption Spectra given below are consistent for the hydrochloride salt of the structure depicted by the formula

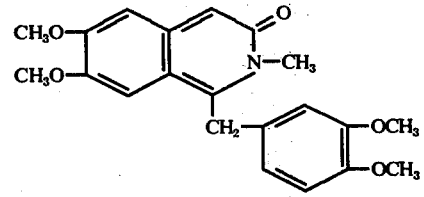

Ultraviolet: λ max (95% ethanol), 400 (ε, 6300); 318 (ε, 4500); 305 (ε, 4500), 258 (ε, 63500); 229 (ε, 23000) millimicrons.

NMR: δ (DMSO-$d_6$, tetramethylsilane reference), 3.7–4.2 (5s, 15, N-$CH_3$, $OCH_3$), 4.9 (s, 2, $CH_2$), 6.3–7.2 (3ArH), 7.3–7.6 (3ArH).

B. Cyclization of ketoacid with methylamine acetate.

3,4-Dimethoxyphenylacetic acid (125 g., 0.637 mole) is added in one portion to 500 ml. of polyphosphoric acid at 75° C. The reaction mixture is then stirred for 15 minutes and quenched in 4 liters of water. After the mixture stands overnight, the tacky yellow brown solid which forms is collected, washed with water and dried to provide 114 g. of product having a melting point of 140°–145° C. Crystallization of this material from ethyl acetate with decolorizing charcoal yields 69.3 g. (58%) of the ketoacid 4,5-dimethoxy-2-[(3,4-dimethoxyphenyl)acetyl]phenylacetic acid, m.p. 150°-153° C.

A mixture of the ketoacid (7.5 g., 0.02 mole), methylamine acetate (9.1 g., 0.1 mole) in 25 ml. of glacial acetic acid is refluxed for 2 hr. and then quenched in 500 ml. of water. This mixture is extracted with chloroform, the chloroform extract dried over magnesium sulfate, stirred with decolorizing charcoal and filtered. Concentration of the filtrate in vacuo provides an oil which is taken up in ethyl acetate and acidified to a pH of 2 with 5N ethanolic hydrogen chloride. The resulting solid is collected and crystallized from methanol-ethyl acetate to provide analytically pure 6,7-dimethoxy-2-methyl-1-veratryl-3(2H)-isoquinolone hydrochloride, m.p. 234°-236° C. (dec.)(uncorr.).

Analysis. Calcd. for $C_{21}H_{23}NO_5 \cdot HCl$ (percent): C, 62.14; H, 5.96; N, 3.45; Cl, 8.74. Found (percent: C, 62.00; H, 6.21; N, 3.61; Cl, 8.57.

C. Condensation of lactone with methylamine.

A mixture of the ketoacid 4,5-dimethoxy-2-[(3,4-dimethoxyphenyl)acetyl]phenylacetic acid (10.0 g., 0.0267 mole), 17 ml. of acetic anhydride, 17 ml. of glacial acetic acid and 2 drops of concentrated sulfuric acid is heated at steam bath temperature for 4 hr. After standing at room temperature overnight the mixture is filtered and the filter cake washed with ether and air dried to provide 7.0 g. (74%) of the lactone 1-(3,4-dimethoxybenzylidene)-6,7-dimethoxy-3-isochromanone as a white solid, m.p. 162°-165° C.

The lactone (3.6 g., 0.01 mole) is suspended in 100 ml. of dry tetrahydrofuran and gaseous methylamine is passed therein until complete solution is obtained. The mixture is left standing overnight at room temperature and concentrated under reduced pressure to provide a residual oil which is taken up in methanol and acidified with 5N ethanolic hydrogen chloride. The acidified solution is cooled and the precipitated solid is collected and crystallized from methanol-ethyl acetate to provide 3.1 g. (76.5%) of 6,7-dimethoxy-2-methyl-1-veratryl-3(2H)-isoquinolone hydrochloride, m.p. 233°-236° C. (dec.)(uncorr.).

EXAMPLE 2

6,7-Diethoxy-2-Methyl-1-(3,4-Diethoxy)Benzyl-3(2H)-Isoquinolone Hydrochloride Following the procedure of Example 1B but substituting 3,4-diethoxyphenylacetic acid in lieu of 3,4-dimethoxyphenylacetic acid there is obtained 6,7-diethoxy-1-(3,4-diethoxy)benzyl-3(2H)-isoquinolone hydrochloride, m.p. 182.5°-187.5° C. (dec.)(corr.) from ethyl acetate.

Analysis. Calcd. for $C_{25}H_{31}NO_5 \cdot HCl$ (percent): C, 64.99; H, 6.98; N, 3.03. Found (percent): 64.71; H, 6.82; N, 3.19.

Ultraviolet: λ max (95% EtOH), 400 (ε, 6200); 320 (ε, 5500); 307 (ε, 5400); 258 (ε, 67000)millimicrons.

NMR: δ (deuterochloroform, tetramethylsilane reference), 1.4 (t, 12, $CH_3$); 3.8 (s, 3, $NCH_3$), 3.9 (q, 8, $CH_2O$); 4.6 (s, 2, $CH_2$); 6.2-7.2 (6, ArH).

EXAMPLE 3

2-Ethyl-6,7-Dimethoxy-1-Veratryl-3(2H)-Isoquinolone Hydrochloride

Following the procedure of Example 1B, but substituting ethylamine acetate (m.p. 85°-90° C.) for methylamine acetate there is obtained 2-ethyl-6,7-dimethoxy-1-veratryl-3(2H)-isoquinolone hydrochloride, as a yellow solid, m.p. 219.5°-221.5° C. (dec.)(corr.).

Analysis. Calcd. for $C_{22}H_{25}NO_5 \cdot HCl$ (percent): C, 62.94; H, 6.24; N, 3.34. Found (percent): C, 63.06; H, 6.28; N, 3.29.

Ultraviolet: λ max (95% EtOH), 402 (ε, 5400); 319 (ε, 4300); 306 (ε, 4600); 258 (ε, 60500) millimicrons.

NMR: δ (DMSO-$d_6$, tetramethylsilane reference), 1.3 (t, 3, $CH_3$); 3.8-4.0 (12, $OCH_3$), 4.6 (q, 2, $NCH_2$); 5.0 (s, 2, $CH_2$); 6.6-7.8 (6, ArH); 10.5 (1, H$^+$).

EXAMPLE 4

2-Allyl-6,7-Dimethoxy-1-veratryl-3(2H)-Isoquinolone Hydrochloride

Following the procedure of Example 1C while employing a 1:3 molar ratio of the lactone to allylamine there is obtained 2-allyl-6,7-dimethoxy-1-veratryl-3(2H)-isoquinolone hydrochloride as a yellow solid, m.p. 182.5°-184.5° C. (dec.)(corr.).

Analysis. Calcd. for $C_{23}H_{25}NO_5 \cdot HCl$ (percent): C, 63.96; H, 6.08; N, 3.24. Found (percent): C, 64.16; H, 5.91; N, 3.33.

Ultraviolet: λ max (95% EtOH), 403 (ε, 4900); 319 (ε, 3900); 308 (ε, 3600); 259 (ε, 57000) millimicrons.

NMR: δ (DMSO-$d_6$, tetramethylsilane reference), 3.7-4.0 (12, $OCH_3$); 4.9-5.2 (4, $(CH_2)_2$); 5.4-6.3 (3, —CH=$CH_2$); 6.5-7.6 (6 ArH).

EXAMPLE 5

2-Cyclopropyl-6,7-Dimethoxy-1-Veratryl-3(2H)-Isoquinolone Hydrochloride

Following the procedure of Example 1C while employing 0.03 mole of the lactone and 0.088 mole of cyclopropylamine there is obtained 10.7 g. (82.5%) of 2-cyclopropyl-6,7-dimethoxy-1-veratryl-3(2H)-isoquinolone hydrochloride as a yellow solid, m.p. 214.0°-215.0° C. (dec.)(corr.).

Analysis. Calcd. for $C_{23}H_{25}NO_5 \cdot HCl$ (percent): C, 63.96; H, 6.07; N, 3.24. Found (percent): C, 63.73; H, 6.12; N, 3.07.

Ultraviolet: λ max (95% EtOH), 400 (ε, 5400); 320 (ε, 5200); 308 (ε, 4800); 258 (ε, 64400); 229 (ε, 23300) millimicrons.

NMR: δ (DMSO-$d_6$, tetramethylsilane reference), 1.3 (m, 4, $(CH_2)_2$); 3.3-4.0 (13, $OCH_3$, CH); 5.1 (s, 2, $CH_2$); 6.4-7.6 (6, ArH); 8.3 (1, H$^+$).

EXAMPLE 6

2-Benzyl-6,7-Dimethoxy-1-Veratryl-3(2H)-Isoquinolone Hydrochloride

Following the procedure of Example 1B but substituting benzylamine acetate for methylamine acetate there is obtained 2-benzyl-6,7-dimethoxy-1-veratryl-3(2H)-isoquinolone hydrochloride as a yellow solid, melting at 145.0° C., resolidifying and melting again at 208.5°-209.5° C. (dec.)(corr.).

Analysis. Calcd. for $C_{27}H_{27}NO_5 \cdot HCl$ (percent): C, 67.28; H, 5.86; N, 2.91. Found (percent): C, 67.10; H, 5.96; N, 2.94.

Ultraviolet: λ max (95% EtOH), 400 (ε, 5300); 320 (ε, 5300); 308 (ε, 4900); 260 (ε, 61700) millimicrons.

NMR: δ (DMSO-$d_6$, tetramethylsilane reference), 3.8-4.1 (12, $OCH_3$); 4.7 (s, 2, $CH_2$); 5.7 (s, 2, $NCH_2$); 6.4-8.0 (11, ArH); 8.5 (1, H$^+$).

EXAMPLE 7

6,7-Dimethoxy-2-(3,4-Dimethoxyphenethyl)-1-Veratryl-3(2H)-Isoquinolone Hydrochloride A mixture of 4,5-dimethoxy-2-[(3,4-dimethoxyphenyl)acetyl]phenylacetic acid (10 g., 0.027 mole) and 3,4-dimethoxyphenethylamine carbonate (24 g., 0.106 mole) is refluxed for 4 hrs. and then quenched with 900 ml. of ice water. Adjustment of the pH of the solution to 6 with concentrated ammonium hydroxide and chilling affords 10 g. of white solid. The solid is taken up in 200 ml. of ethyl acetate, dried over magnesium sulfate and treated with decolorizing charcoal. Acidification of the solution with 5N ethanolic hydrogen chloride and chilling for 3 hr. in ice water provides 9 g. of white solid, m.p. 226°–229° C. This material is fractionally crystallized from methanol-ethanol-water (17:2:1) to give 6.1 g. of a white solid, m.p. 238°–248° C. (dec.) and 1.9 g. of yellow solid, m.p. 218°–220° C. (dec.). Crystallization of the yellow solid from isopropanol yields 1.5 g. of 6,7-dimethoxy-2-(3,4-dimethoxyphenethyl)-1-veratryl-3(2H)-isoquinolone hydrochloride as a yellow powder melting at 215.5°–219.0° C. (dec.) (corr.).

Analysis. Calcd. for $C_{30}H_{33}NO_7 \cdot HCl$ (percent): C, 64.80; H, 6.16; N, 2.52. Found (percent): C, 65.07; H, 6.12; N, 2.72.

Ultraviolet: λ max (95% EtOH), 400 (ε, 6500); 320 (ε, 6100); 308 (ε, 5700); 259 (ε, 72300); 230 (ε, 33200) millimicrons.

NMR: δ (deuterochloroform, tetramethylsilane reference), 3.1 (m, 2, $CH_2$); 3.8–4.1 (4s, 18, $OCH_3$); 4.5 (m, 2, $CH_2$); 4.6 (s, 2, $CH_2$); 6.4–7.2 (8, ArH); 8.3 (1, ArH).

EXAMPLE 8

2-Amino-6,7-Dimethoxy-1-Veratryl-3(2H)-Isoquinolone Hydrochloride

Following the procedure of Example 1B but substituting hydrazine hydrate for methylamine acetate there is obtained 2-amino-6,7-dimethoxy-1-veratryl-3(2H)-isoquinolone hydrochloride as a yellow solid, m.p. 206.0°–207.0° C. (dec.)(corr.).

Analysis. Calcd. for $C_{20}H_{22}N_2O_5 \cdot HCl$ (percent): C, 59.04; H, 5.70; N, 6.89. Found (percent): C, 59.32; H, 5.84; N, 6.77.

Ultraviolet: λ max (95% EtOH), 400 (ε, 6400); 318 (ε, 5100); 307 (ε, 4900); 247 (ε, 64200) millimicrons.

NMR: δ (DMSO-$d_6$, tetramethylsilane reference), 3.8–4.0 (12, $OCH_3$); 5.0 (s, 2, $CH_2$); 6.9–7.5 (6, ArH); 8.2 (s, 3, $NH_3+$).

EXAMPLE 9

2-Hydroxy-6,7-Dimethoxy-1-Veratryl-3-(2H)-Isoquinolone Hydrochloride

Aqueous sodium hydroxide (20 ml. of 5.15N) added to a suspension of 4,5-dimethoxy-2-[(3,4-dimethoxyphenyl)acetyl]phenylacetic acid (10.0 g., b 0.0267 mole) and hydroxylamine hydrochloride (4.9 g., 0.07 mole) in 50 ml. of water provides a clear solution which is heated for 1 hr. at 90° C. The solution is stirred with decolorizing charcoal, filtered, acidified to a pH of 3 with concentrated hydrochloric acid, and then chilled to provide an amber gum which is separated by decanting the supernatent liquid. Triturating the gum with ethyl acetate affords 2-(3,4-dimethoxyphenylacetyl)-4,5-dimethoxyphenylacetic acid oxime, m.p. 134°–138° C.

The oxime (2.6 g., 0.0066 mole) taken up in 100 ml. of acetic acid and 2 ml. of concentrated hydrochloric acid and stirred for 16 hr. Concentration of the filtrate in vacuo affords a residue which is crystallized first from ethanol-ethyl acetate and then methanol to provide analytically pure 3.7 g. of 2-hydroxy-6,7-dimethoxy-1-veratryl-3(2H)-isoquinolone hydrochloride as a yellow solid, m.p. 205.5°–210.0° C. (dec.)(corr.).

Analysis. Calcd. for $C_{20}H_{21}NO_6 \cdot HCl$ (percent): C, 58.89; H, 5.44; N, 3.43; Cl, 8.69. Found (percent): C, 59.16; H, 5.31; N, 3.61; Cl, 8.67.

Ultraviolet: λ max (95% EtOH), 394 (ε, 4400); 310 sh (ε, 4400); 256 (ε, 38000) millimicrons.

NMR: δ (DMSO-$d_6$, tetramethylsilane reference), 3.8–4.0 (12, $OCH_3$); 4.9 (s, 2, $CH_2$); 6.9–7.6 (6, ArH); 10.5 (s, 2,OH, $H^+$).

EXAMPLE 10

3,6,7-Trimethoxy-1-Veratrylisoquinoline Hydrochloride

A suspension of 6,7-dimethoxy-1-veratryl-3-isoquinolinol (3.6 g., 0.01 mole) in a mixture of 70 ml. of water and 20 ml. of 1N sodium hydroxide is stirred at 25° C. until the yellow isoquinolinol has turned white and the supernatent is colorless. The suspension is chilled, filtered, and the filter cake washed with 50 ml. of tetrahydrofuran. Air drying provides 4.0 g. (100%) of 6,7-dimethoxy-1-veratryl-3-isoquinolinol sodium salt as a white solid monohydrate, sintering at 250°–260° C.

The sodium salt of 6,7-dimethoxy-1-veratryl-3-isoquinolinol (1.0 g., 0.0025 mole) is suspended in 20 ml. of absolute ethanol and 2% silver nitrate/ethanol is added dropwise thereto until further addition causes no more yellow-orange precipitate to form. The resulting suspension is stirred at 25° C. for 1 hr. in the dark and filtered. The yellow filter cake is washed first with 5 ml. of absolute ethanol then with 20 ml. of ether and air dried to provide 1 g. of 6,7-dimethoxy-1-veratryl-3-isoquinolinol silver salt.

Methyl iodide (34 g., 0.24 mole) is added to the silver salt in 15 ml. of ether and the mixture stirred for 16 hr. in the dark. Dilution of the mixture with 125 ml. of tetrahydrofuran, filtering and concentrating the filtrate provides a solid residue. Crystallization of the residue from ether-methylene chloride affords 0.5 g. (49%) of 3,6,7-trimethoxy-1-veratrylisoquinoline free base as pale yellow crystals, m.p. 135°–136° C.

The hydrochloride salt prepared by acidifying the free base with ethanolic hydrogen chloride is crystallized from methanol-isopropanol to analytically pure 3,6,7-trimethoxy-1-veratrylisoquinoline hydrochloride as a pale yellow solid, melting at 190.5°–194.0° C. (dec.)(corr.).

Analysis. Calcd. for $C_{21}H_{23}NO_5 \cdot HCl$ (percent): C, 62.14; H, 5.96; N, 3.45. Found (percent): C, 62.37; H, 6.00; N, 3.36.

Ultraviolet: λ max (95% EtOH), 345 (ε, 5700); 272 (ε, 6900); 240 (ε, 60600) millimicrons.

NMR: δ (DMSO-$d_6$, tetramethylsilane reference), s, 3.8–4.1 (5s, 15, $OCH_3$); 4.5 (s, 2, $CH_2$); 6.9–7.3 (6, ArH).

EXAMPLE 11

3-Ethoxy-6,7-Dimethoxy-1-Veratrylisoquinoline

Triethyloxonium fluoroborate prepared from boron fluoride etherate (6.81 g., 0.048 mole) and epichlorohydrin (3.33 g., 0.036 mole) according to the method of H. Meerwin, Org. Syn., 46, 113 (1966) is taken up in 100 ml. of dry methylene chloride and 6,7-dimethoxy-1-veratryl-3-isoquinolinol (10.8 g., 0.03 mole) in 200 ml. of methylene chloride added thereto. The mixture is stirred at 25° C. for 16 hr., chilled and washed first with aqueous potassium carbonate and then with three 200 ml. portions of water. After drying the washed methylene chloride solution over magnesium sulfate and treating with decolorizing charcoal, the solvent is evaporated. Crystallization of the residue first from methanol-isopropyl alcohol and then from acetonitrile and finally again from methanol-isopropyl alcohol affords 4.1 g. (43%) of analytically pure 3-ethoxy-6,7-dimethoxy-1-veratrylisoquinoline as a white solid, m.p. 110.0°–112.0° C. (corr.).

Analysis. Calcd. for $C_{22}H_{25}NO_5$ (percent): C, 68.92; H, 6.57; N, 3.65. Found (percent): C, 69.05; H, 6.53; N, 3.71.

Ultraviolet: λ max ($CHCl_3$), 348 (ε, 5500); 273 (ε, 7300); 243 (ε, 55200) millimicrons.

NMR: δ (deuterochloroform, tetramethylsilane reference), 1.3 (t, 3, $CH_3$); 3.7–4.0 (4s, 12, $OCH_3$); 4.4 (N, 2, $OCH_2$); 4.5 (s, 2, $CH_2Ar$); 6.7–7.4 (6, ArH).

EXAMPLE 12

3-Benzyloxy-6,7-Dimethoxy-1-Veratrylisoquinoline

A mixture of 6,7-dimethoxy-1-veratryl-3-isoquinolinol (3.6 g., 0.01 mole), benzyl bromide (1.71 g., 0.01 mole, 1.2 ml.) powdered anhydrous potassium carbonate (2.8 g., 0.02 mole) in 100 ml. of acetone is refluxed for 72 hr. and filtered. The filtrate is concentrated under reduced pressure and the resulting residue stirred with petroleum ether (b.p. 30°–60° C.) to provide a solid. Crystallization from a mixture of methanol-acetone-isopropanol (with decolorizing charcoal) affords 3.2 g. of analytically pure 3-benzyloxy-6,7-dimethoxy-1-veratrylisoquinoline, m.p. 114.0°–115.5° C. (corr.).

Analysis. Calcd. for $C_{27}H_{27}NO_5$ (percent): C, 72.79; H, 6.11; N, 3.14. Found (percent): C, 72.72; H, 6.04; N, 3.14.

Ultraviolet: λ max ($CHCl_3$), 348 (ε, 5500); 244 (ε, 60600) millimicrons.

NMR: δ (deuterochloroform, tetramethylsilane reference), 3.6–3.9 (4s, 12, $OCH_3$); 4.4 (s, 2, $CH_2$); 5.4 (s, 2, $OCH_2$); 6.7–7.3 (11, ArH).

EXAMPLES 13–46.

Additional exemplification of the compounds of the present invention are provided in the following Tables I and II. These compounds are obtained according to the procedures hereinabove described in Examples 1–10 from the indicated reactants.

TABLE I

ADDITIONAL ISOQUINOLINES

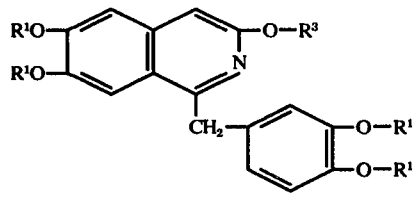

| Ex. No. | $R^1$ | $R^3$ | Reactants |
|---|---|---|---|
| 13 | $CH_3$ | $(CH_3)_2CH-$ | 6,7-dimethoxy-1-veratryl-3-isoquinolinol and triisopropyloxonium fluoroborate |
| 14 | $CH_3$ | $n-C_4H_9-$ | 6,7-dimethoxy-1-veratryl-3-isoquinolinol, n-butylbromide and potassium carbonate |
| 15 | $CH_3$ | $(CH_3)_3C-$ | 6,7-dimethoxy-1-veratryl-3-isoquinolinol, tert-butyl-bromide and potassium carbonate |
| 16 | $C_2H_5$ | $CH_3-$ | 6,7-diethoxy-1-(3,4-diethoxy-benzyl)-3-isoquinolinol and trimethyloxonium fluoroborate |
| 17 | $(CH_3)_2CH-$ | $CH_3-$ | 6,7-diisopropoxy-1-(3,4-diisopropoxybenzyl)-3-isoquinolinol and trimethyloxonium fluoroborate |
| 18 | $n-C_4H_9$ | $CH_3-$ | 6,7-di-n-butoxy-1-(3,4-di-n-butoxybenzyl)-3-isoquinolinol and trimethyloxonium fluoroborate |
| 19 | $CH_3$ | $CH_2=CHCH_2-$ | 6,7-dimethoxy-1-veratryl-3-isoquinolinol, allyl bromide and potassium carbonate |
| 20 | $CH_3$ | ⬜ | 6,7-dimethoxy-1-veratryl-3-isoquinolinol, cyclobutyl bromide and potassium carbonate |

TABLE II
ADDITIONAL ISOQUINOLONES

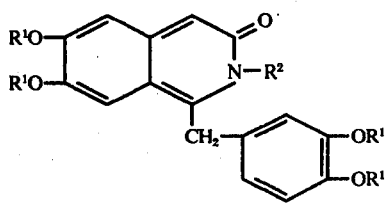

| Ex. No. | $R^1$ | $R^2$ | Reactants |
|---|---|---|---|
| 21 | $C_2H_5$ | $CH_3$ | 1-(3,4-diethoxybenzylidene)-6,7-diethoxy-3-isochromanone and methylamine |
| 22 | $(CH_3)_2CH$ | $CH_3$ | 1-(3,4-diisopropoxybenzylidene)-6,7-diisopropoxy-3-isochromanone and methylamine |
| 23 | $n\text{-}C_4H_9$ | $CH_3$ | 1-(3,4-di-n-butoxybenzylidene)-6,7-di-n-butoxy-3-isochromanone and methylamine |
| 24 | $CH_3$ | cyclobutyl | 1-(3,4-dimethoxybenzylidene)-6,7-dimethoxy-3-isochromanone and cyclobutylamine |
| 25 | $CH_3$ | cyclopentyl | 1-(3,4-dimethoxybenzylidene)-6,7-dimethoxy-3-isochromanone and cyclopentylamine |
| 26 | $CH_3$ | $(CH_3)_2CH$ | 1-(3,4-dimethoxybenzylidene)-6,7-dimethoxy-3-isochromanone and isopropylamine |
| 27 | $CH_3$ | $n\text{-}C_4H_9$ | 1-(3,4-dimethoxybenzylidene)-6,7-dimethoxy-3-isochromanone and n-butylamine |
| 28 | $CH_3$ | $C_6H_5\text{-}CH_2CH(CH_3)\text{-}$ | 1-(3,4-dimethoxybenzylidene)-6,7-dimethoxy-3-isochromanone and α-methylphenethylamine |
| 29 | $CH_3$ | $C_6H_5\text{-}CH_2C(CH_3)_2\text{-}$ | 1-(3,4-dimethoxybenzylidene)-6,7-dimethoxy-3-isochromanone and phenyl-t-butylamine |
| 30 | $CH_3$ | $Cl\text{-}C_6H_4\text{-}CH_2CH_2\text{-}$ | 1-(3,4-dimethoxybenzylidene)-6,7-dimethoxy-3-isochromanone and 4-chlorophenethylamine |
| 31 | $CH_3$ | 2-Br-$C_6H_4$-$CH_2$- | 1-(3,4-dimethoxbenzylidene)-6,7-dimethoxy-3-isochromanone and 2-bromobenzylamine |
| 32 | $CH_3$ | $CH_3\text{-}C_6H_4\text{-}CH_2\text{-}$ | 1-(3,4-dimethoxybenzylidene)-6,7-dimethoxy-3-isochromanone and 4-methylbenzylamine |
| 33 | $CH_3$ | $(CH_3)_2CH\text{-}C_6H_4\text{-}CH_2\text{-}$ | 1-(3,4-dimethoxybenzylidene)-6,7-dimethoxy-3-isochromanone and 4-isopropylbenzylamine |
| 34 | $CH_3$ | 3,4-methylenedioxybenzyl | 1-(3,4-dimethoxybenzylidene-6,7-dimethoxy-3-isochromanone and 3,4-methylenedioxybenzylamine |
| 35 | $CH_3$ | 1-(3,4-methylenedioxyphenyl)isopropyl | 1-(3,4-dimethoxybenzylidene)-6,7-dimethoxy-3-isochromanone and 1-(3,4-methylenedioxyphenyl)isopropylamine |
| 36 | $CH_3$ | $CH_3O\text{-}C_6H_4\text{-}CH_2\text{-}$ | 1-(3,4-dimethoxybenzylidene)-6,7-dimethoxy-3-isochromanone and 4-methoxybenzylamine |
| 37 | $CH_3$ | 2-$OCH_3$-$C_6H_4$-$CH_2$- | 1-(3,4-dimethoxybenzylidene)-6,7-dimethoxy-3-isochromanone and 2-methoxybenzylamine |
| 38 | $CH_3$ | $(CH_3)_2CHO\text{-}C_6H_4\text{-}CH_2\text{-}$ | 1-(3,4-dimethoxybenzylidene)-6,7-dimethoxy-3-isochromanone and 4-isopropoxybenzylamine |

TABLE II-continued
ADDITIONAL ISOQUINOLONES

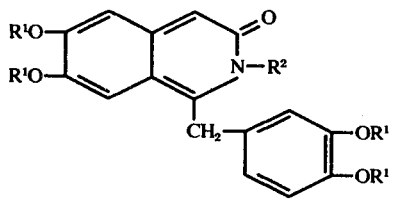

| Ex. No. | R¹ | R² | Reactants |
|---|---|---|---|
| 39 | $CH_3$ | 3,4,5-trimethoxybenzyl | 1-(3,4-dimethoxybenzyl-idene)-6,7-dimethoxy-3-isochromanone and 3,4,5-trimethoxybenzylamine |
| 40 | $CH_3$ | 2,3-dimethoxybenzyl | 1-(3,4-dimethoxybenzyl-idene-6,7-dimethoxy-3-isochromanone and 2,3-dimethoxybenzylamine |
| 41 | $CH_3$ | $CH_3O-$ | 1-(3,4-dimethoxybenzyl-idene)-6,7-dimethoxy-3-isochromanone and methoxyamine |
| 42 | $CH_3$ | $(CH_3)_2CHO-$ | 1-(3,4-dimethoxybenzyl-idene)-6,7-dimethoxy-3-isochromanone and isopropoxyamine |
| 43 | $CH_3$ | $CH_3NH-$ | 1-(3,4-dimethoxybenzyl-idene)-6,7-dimethoxy-3-isochromanone and N-methylhydrazine |
| 44 | $CH_3$ | $(CH_3)_2CHNH-$ | 1-(3,4-dimethoxybenzyl-idene)-6,7-dimethoxy-3-isochromanone and N-isopropylhydrazine |
| 45 | $CH_3$ | $(CH_3)_2N-$ | 1-(3,4-dimethoxybenzyl-idene)-6,7-dimethoxy-3-isochromanone and N,N-dimethylhydrazine |
| 46 | $CH_3$ | $(n-C_4H_9)_2N-$ | 1-(3,4-dimethoxybenzyl-idene)-6,7-dimethoxy-3-isochromanone and N,N-di-n-butylhydrazine |

It will be appreciated by those skilled in the art that specific embodiments disclosed in the foregoing specification are exemplary of other modifications which can be made without departing from the spirit and scope of the appended claims.

What is claimed is:

1. A process for eliciting a hypotensive and vasodilating effect in a mammal in need thereof which comprises systemic administration to said mammal a nontoxic effective dose of from about 0.05 to 20 mg./kg. of body weight of said mammal of a compound selected from the group consisting of those having the formula

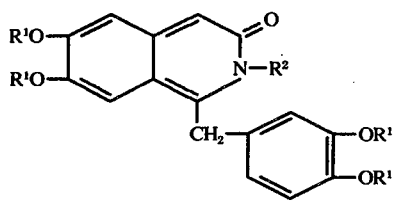

wherein
R¹ is lower alkyl having up to 4 carbon atoms;
R² is selected from the group consisting of hydroxy, amino, lower alkylamino having up to 4 carbon atoms, lower dialkylamino having up to 4 carbon atoms, lower alkyl having up to 4 carbon atoms, alkenyl having from 3 to 6 carbon atoms, cycloalkyl having from 3 to 5 carbon atoms, phenylalkyl having up to 10 carbon atoms and substituted phenylalkyl having up to 10 carbon atoms apart from the substituent, said substituent being in the 2-, 3-, 4-, 5-, or 6-ring positions and being selected from the group consisting of halogen, lower alkyl having up to 4 carbon atoms, and methylenedioxy, or from 1 to 3 lower alkoxy groups having up to 4 carbon atoms each;
and a pharmaceutically acceptable acid addition salt thereof.

2. The process as claimed in claim 1 wherein the isoquinolone compound employed is 6,7-dimethoxy-2-methyl-1-veratryl-3(2H)-isoquinolone.

3. The process as claimed in claim 1 wherein the isoquinolone compound employed is 6,7-dimethoxy-2-methyl-1-veratryl-3(2H)-isoquinolone hydrochloride.

4. The process as claimed in claim 1 wherein the isoquinolone compound employed is 6,7-diethoxy-2-methyl-1-(3,4-diethoxy)benzyl-3(2H)-isoquinolone.

5. The process as claimed in claim 1 wherein the isoquinolone compound employed is 6,7-diethoxy-2-methyl-1-(3,4-diethoxy)benzyl-3(2H)-isoquinolone hydrochloride.

6. The process as claimed in claim 1 wherein the isoquinolone compound employed is 2-allyl-6,7-dimethoxy-1-veratryl-3(2H)-isoquinolone.

7. The process as claimed in claim 1 wherein the isoquinolone compound employed is 2-ethyl-6,7-dimethoxy-1-veratryl-3(2H)-isoquinolone.

8. The process as claimed in claim 1 wherein the isoquinolone compound employed is 2-cyclopropyl-6,7-dimethoxy-1-veratryl-3(2H)-isoquinolone.

9. The process as claimed in claim 1 wherein the isoquinolone compound employed is 2-cyclopropyl-6,7-dimethoxy-1-veratryl-3(2H)-isoquinolone hydrochloride.

10. The process as claimed in claim 1 wherein the isoquinolone compound employed is 2-benzyl-6,7-dimethoxy-1-veratryl-3(2H)-isoquinolone.

11. The process as claimed in claim 1 wherein the isoquinolone compound employed is 6,7-dimethoxy-2-(3,4-dimethoxyphenethyl)-1-veratryl-3(2H)-isoquinolone.

12. The process as claimed in claim 1 wherein the isoquinolone compound employed is 2-amino-6,7-dimethoxy-1-veratryl-3(2H)-isoquinolone.

13. The process as claimed in claim 1 wherein the isoquinolone compound employed is 2-amino-6,7-dimethoxy-1-veratryl-3(2H)-isoquinolone hydrochloride.

14. The process as claimed in claim 1 wherein the isoquinolone compound employed is 2-hydroxy-6,7-dimethoxy-1-veratryl-3(2H)-isoquinolone.

15. The process as claimed in claim 1 wherein the isoquinolone compound employed is the isoquinolone of the formula

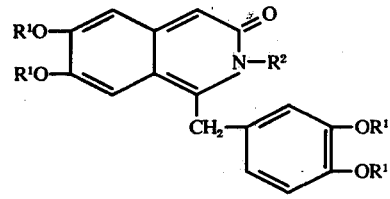

wherein $R^1$ is $n-C_4H_9$ and $R^2$ is $CH_3$.

* * * * *